United States Patent [19]

Kelder

[11] 4,348,390

[45] Sep. 7, 1982

[54] NOVEL BIS- AND MONO-QUATERNARY AMMONIUM DERIVATIVES OF 2β,16β-DIPIPERIDINO-5α-ANDROSTANES, PROCESSES FOR THEIR PREPARATION AND PHARMACEUTICAL PREPARATIONS

[75] Inventor: Jan Kelder, Oss, Netherlands
[73] Assignee: AKZO nv, Oss, Netherlands
[21] Appl. No.: 214,650
[22] Filed: Dec. 10, 1980

[30] Foreign Application Priority Data

Dec. 12, 1979 [GB] United Kingdom ................. 7942883

[51] Int. Cl.³ ........................ A61K 31/58; C07J 43/00
[52] U.S. Cl. ................................. 424/241; 260/239.5
[58] Field of Search ...................... 260/239.5; 424/241

[56] References Cited

U.S. PATENT DOCUMENTS 4,237,126 12/1980 Carlyle et al. ...................... 424/241
4,297,351 10/1981 Carlyle et al. ...................... 424/241

OTHER PUBLICATIONS

W. R. Buckett et al., Pancuronuim Bromide and Neuromuscular Blocking Agents Containing Acetyl-Choline Fragments, J. Med. Chem. 16 (10) at 1116 to 1123 (1973).

Primary Examiner—Elbert L. Roberts
Attorney, Agent, or Firm—Abelman, Frayne & Rezac

[57] ABSTRACT

The invention relates to novel bisquaternary ammonium derivatives of 2β,16β-dipiperidino-5α-androstanes having the formula:

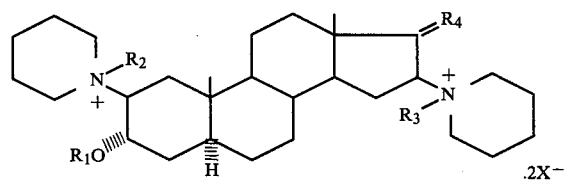

.2X⁻ wherein

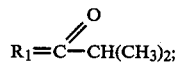

$R_1 = C - CH(CH_3)_2$;

$R_2 = CH_3$, $C_2H_5$ or $CH_2CH=CH_2$; $R_3 = CH_3$, $C_2H_5$ or $CH_2CH=CH_2$, with the proviso that $R_2$ and $R_3$ are not $CH_3$ simultaneously; $R_4 = O$ or $H(\beta OR_5)$, wherein $R_5 = H$ or aliphatic carbacyl (1–6 C); and $X = $ a halogen atom, to processes for their preparation and to pharmaceutical preparations. The invention also relates to novel 16-monoquaternary analogs as intermediates.

The compounds possess neuromuscular blocking activity.

6 Claims, No Drawings

NOVEL BIS- AND MONO-QUATERNARY AMMONIUM DERIVATIVES OF 2β,16β-DIPIPERIDINO-5α-ANDROSTANES, PROCESSES FOR THEIR PREPARATION AND PHARMACEUTICAL PREPARATIONS

This invention relates to novel bis- and mono-quaternary ammonium derivatives of 2β,16β-dipiperidino-5α-androstanes, to processes for their preparation and to pharmaceutical preparations containing one or more of said androstane compounds as active constituent.

Bis- and mono-quaternary ammonium derivatives of 2β,16β-dipiperidino-5α-androstanes are known from e.g. British Patent Specifications 1 138 605 and 1 454 749. See also Journal of Medicinal Chemistry 16, 1116–1124, (1973). These compounds have neuromuscular blocking activity. A well-known compound of this type is pancuronium bromide (3α,17β-diacetoxy-2β,16β-dipiperidino-5α-androstane dimethobromide), which has proved a clinically useful non-depolarising muscle relaxant of medium duration of action.

Surprisingly, it was found that novel bis-quaternary ammonium derivatives of 2β,16β-dipiperidino-5α-androstanes, having the formula I:

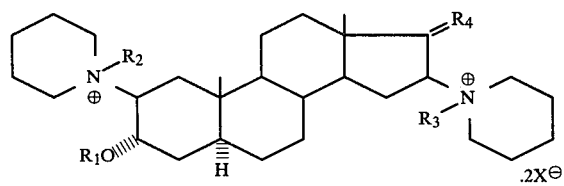

wherein
$R_1 =$

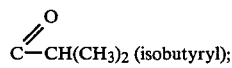

C—CH(CH$_3$)$_2$ (isobutyryl);

$R_2$ = methyl, ethyl or allyl, preferably allyl;

$R_3$ = methyl, ethyl or allyl, preferably ethyl, and with the proviso that $R_2$ and $R_3$ are not methyl simultaneously;

$R_4$ = O or H(βOR$_5$), wherein $R_5$ = H or aliphatic carbacyl (1–6 C), preferably acetyl; and X = a halogen atom, preferably Br, are very potent neuromuscular blocking agents with a quick onset of action, a relatively short duration of action and a quick recovery time. Very remarkable is the short duration and the high ratio between onset time and recovery time. Moreover the novel compounds show a high selectively, i.e. have a favourable ratio of neuromuscular activity and unwanted vagolytic activity, and neither affect the cardiovascular system, nor release histamine to the same extent as the muscle-relaxant d-tubocurarine.

Therefore, the present invention relates to the novel compound having the above formula and also extends to processes for their preparation. The invention also relates to pharmaceutical compositions containing a pharmaceutically effective amount of one or more of the novel compounds having the above formula.

The compounds according to the invention can be prepared by methods employing steps known or obvious to those skilled in the art.

Suitable starting substances include 2β,16β-dipiperidino-3α-hydroxy-5α-androstan-17-one and 2β,16β-dipiperidino-5α-androstane-3α,17β-diol which can be prepared according to the methods described in British Patent Specification No. 1 138 605.

These starting substances are esterified in position 3 with isobutyric acid, preferably with a functional derivative thereof, such as the anhydride or the acid chloride, and if desired in a suitable solvent, such as methylene chloride or pyridine. Esterification of the 3α-hydroxy-17-ketone gives the 3α-isobutyrate, whereas esterification of the 3α,17β-diol results in the 3α,17β-diisobutyrate. For obtaining the 3α-isobutyrate with a different ester group in 17β-position the 3α-isobutyroxy-17-ketone is reduced e.g. with a complex metal hydride such as potassium borohydride, lithium aluminium hydride, sodium triethoxy aluminium hydride or sodium trimethoxy borohydride, in a suitable solvent, e.g. t-butanol, whereafter the 3α-isobutyroxy-17β-ol is esterified with an aliphatic carbacylic acid having 1–6 carbon atoms, e.g. acetic acid, butyric acid, valeric acid, caproic acid, trimethyl acetic acid, or a functional derivative thereof, such as the anhydride or the acid chloride.

The 2β,16β-bispiperidino-3α-isobutyroxy-17-ketone or -17β-acylates are then reacted with a methyl, ethyl or allyl halide in a suitable solvent, such as methylene chloride or methylcyanide, at room temperature for several days or at an elevated temperature, e.g. 80° C., for 6 to 12 hours. Since the 16-piperidino group is more reactive to quaternarisation than is the 2-piperidino group, the 16-monoquaternary ammonium compound may be prepared by treating the 2β,16β-dipiperidino steroid with a methyl, ethyl or allyl halide in a solvent, e.g. ether, in which the formed 16-monoquaternary ammonium steroid is sparingly soluble. The 16-monoquaternary ammonium compound can then be further treated with a different alkyl halide to give the corresponding 2β,16β-bisquaternary ammonium compound.

The anion in the bisquaternary ammonium derivatives of the invention (X$^-$) is halogen, e.g. Cl$^-$, Br$^-$ or I$^-$, preferably Br$^-$.

The present bisquaternary ammonium compounds are intended particularly for use in clinical practice to produce skeletal muscular paralysis during surgical operations.

The compounds are usually administered by intravenous injection, in initial dosages between 10 and 50 mg (bolus injection), followed if necessary by smaller supplementary dosages.

The compounds have a very short duration of action, which is in the range of 25 to 75% of that of pancuronium bromide. The ratio between onset time and recovery time is in the range of 1 to 10, i.e. recovery times are equal or even shorter than onset times. (For pancuronium bromide the recovery time is longer than the onset time.)

In the preparation of the bisquaternary ammonium compounds of the present invention the 16-monoquaternary ammonium compounds are valuable intermediates. Therefore, the present invention also relates to novel 16-mono-quaternary ammonium compounds having the formula II:

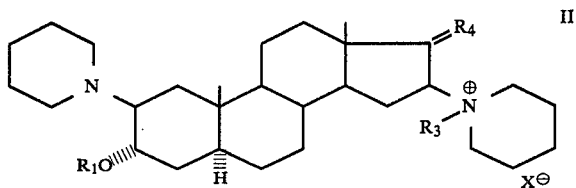

wherein
R₁=

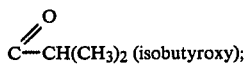

R₃=ethyl or allyl, preferably ethyl;
R₄=O or H(βOR₅), wherein R₅=H or aliphatic carbacyl (1-6 C), preferably acetyl; and
X=a halogen atom, preferably Br.

These compounds are not only important intermediates for preparing bisquaternary ammonium compounds having the formula I, but possess themselves also interesting neuromuscular blocking activities.

The following examples illustrate the invention.

EXAMPLE I (a)
2β,16β-didiperidino-5α-androstane-3α,17β-diol-di-isobutyrate

Isobutyryl chloride (40 ml) was added over 10 minutes to a stirred solution of 2β,16β-dipiperidino-5α-androstane-3α,17β-diol (40 g) in methylene dichloride (200 ml), keeping the reaction temperature at 5° C.±5°. After 16 hours, saturated potassium bicarbonate solution (250 ml) was added, ensuring the final pH was above 7. The methylene dichloride layer was given a further potassium bicarbonate wash followed by water to pH=7. The dried extract after evaporation to dryness in vacuo, afforded a brown gum (52.4 g), which was filtered through a column of acid-washed alumina (2 wt.) in ether to give a pale yellow eluate, which when concentrated (ether evaporation) gave 48.1 g of non-crystalline 3,17-di-isobutyrate.

(b) 2β,16β-Dipiperidino-5α-androstane-3α,17β-diol di-isobutyrate di-ethobromide

Ethyl bromide (10.0 g) was added to a solution of 2β,16β-dipiperidino-5α-androstane-3α,17β-diol di-isobutyrate (4.8 g) in freshly distilled methylene chloride (15 ml). The solution was stored at room temperature and further portions (10.0 g) were added after 7 days and 14 days. The solvents were removed under reduced pressure after a total of 17 days, the residue dissolved in 3:1 ethyl acetate/isopropanol and chromatographed in acid-washed alumina. Elution with isopropanol gave a colourless gum (6.3 g) which was crystallised twice from isopropanol/acetone to give 3.5 g 2β,16β-dipiperidino-5α-androstane-3α,17β-diol di-isobutyrate di-ethobromide.

Using ethyl iodide in place of ethyl bromide the corresponding di-etho-iodide was obtained.

EXAMPLE II (a)
N-methyl-N-(3α,17β-di-isobutyroxy-2β-piperidino-5α-androstan-16β-yl)piperidinium bromide Methylbromide (90 g) was added to a solution of 2β,16β-dipiperidino-5α-androstane-3α,17β-diol di-isobutyrate (30 g) in methylene dichloride (600 ml) in a pressure bottle at 20° C. After 5 hours the reaction mixture was evaporated to dryness in vacuo, taken up in the minimum of methylene dichloride and on addition of ether N-methyl-N-(3α,17β-di-isobutyroxy-2β-piperidino-5α-androstan-16β-yl)piperidinium bromide was precipitated as a pale yellow solid which was filtered and dried (26.5 g).

The filtrate which contained the unquaternised free base, was recycled to afford a further crop (5.4 g) of the title compound. The two crops were combined and crystallised from methylene dichloride/acetone to yield the 16-mono-metho-bromide as an off-white solid (25.4 g).

The following compounds were prepared in a similar manner:
N-ethyl-N-(3α,17β-di-isobutyroxy-2β-piperidino-5α-androstan-16β-yl)piperidinium bromide;
N-allyl-N-(3α,17β-di-isobutyroxy-2β-piperidino-5α-androstan-16β-yl)piperidinium bromide.

(b)
3α,17β-Di-isobutyroxy-2β-(1'-allyl-1'-piperidino)-16β-(1''-methyl-1''-piperidino)-5α-androstane dibromide Freshly distilled allyl bromide (4.0 ml) was added to a solution of N-methyl-N-(3α,17β-di-isobutyroxy-2β-piperidino-5α-androstan-16β-yl)piperidinium bromide (8.0 g) in methylene dichloride (80 ml) in a pressure bottle at 20° C. After 70 hours the reaction mixture was filtrated and the filtrate evaporated to dryness in vacuo. Chromatography and crystallisation from isopropanol/acetone gave 3.8 g 3α,17β-di-isobutyroxy-2β-(1'-allyl-1'-piperidino)-16β-(1''-methyl-1''-piperidino)-5α-androstane dibromide.

The following compounds were prepared in a similar manner:
3α,17β-di-isobutyroxy-2β-(1'-allyl-1'-piperidino)-16β-(1''-ethyl-1''-piperidino)-5α-androstane dibromide;
3α,17β-di-isobutyroxy-2β-(1'-methyl-1'-piperidino)-16β-(1''-ethyl-1''-piperidino)-5α-androstane dibromide.

EXAMPLE III

2β,16β-Di(1'-allyl-1'-piperidino)-5α-androstane-3α,17β-diol di-isobutyrate dibromide In a similar way as described in Example I(b) but using allyl bromide in place of ethyl bromide 2β,16β-dipiperidino-5α-androstane-3α,17β-diol was converted into the title compound.

EXAMPLE IV (a)
3α-Isobutyroxy-2β,16β-dipiperidino-5α-androstan-17-one

Isobutyrylchloride (55 ml) was added over 20 minutes to a stirred solution of 3α-hydroxy-2β,16β-dipiperidino-5α-androstan-17-one (150 g) in methylene dichloride (750 ml), keeping the reaction temperature at 5° C. (±5°).

After 16 hours saturated potassium bicarbonate solution (1.000 ml) was added, ensuring that the final pH was >7. The methylene dichloride layer was given a further potassium bicarbonate wash, followed by water to pH=7. The dried extract after evaporation to dryness in vacuo afforded a brown gum, which was crystallised from ether to give 3α-isobutyroxy-2β,16β-dipiperidino-5α-androstan-17-one (115 g). Recrystallisation from ether yielded the isobutyroxy-17-ketone (103.2 g).

(b) Quaternarisation of 3α-isobutyroxy-2β,16β-dipiperidino-5α-androstan-17-one in a similar way as described in Example I(b) gave the corresponding di-ethobromide, the di-ethochloride and the di-allyloiodide, respectively.

(c) Quaternarisation of 3α-isobutyroxy-2β,16β-dipiperidino-5α-androstan-17-one in a similar way as described in Example II gave the corresponding 2β-(1'-allyl-1'-piperidino)-16β-(1''-methyl-1''-piperidino)-dibromide, 2β-(1'-allyl-1'-piperidino)-16β-(1''-ethyl-1''-piperidino)-dibromide and 2β-(1'-methyl-1'-piperidino)-16β-(1''-ethyl-1''-piperidino)-dibromide, respectively.

EXAMPLE V (a) 2β,16β-Dipiperidino-5α-androstane-3α,17β-diol 3-isobutyrate

Sodium borohydride (16 g) was added to a stirred solution of 3α-isobutyroxy-2β,16β-dipiperidino-5α-androstan-17-one (51.6 g) in methylene dichloride (150 ml) and methanol (150 ml) and the reaction mixture was stirred for a further hour. Water was added, the product extracted with ether, and the extract washed well with water and dried. Concentration of the ether solution yielded 2β,16β-dipiperidino-5α-androstan-3α,17β-diol 3-isobutyrate (21 g) which was recrystallised from ether.

By quaternarisation the di-ethobromide and the 2β-(1'-allyl-1'-piperidino)-16β-(1''-methyl-1''-piperidino)-di-iodide, respectively, were obtained.

EXAMPLE VI (a) 2β,16β-Dipiperidino-5α-androstane-3α,17β-diol 3-isobutyrate 17-acetate A solution of 2β,16β-dipiperidino-5α-androstane-3α,17β-diol 3-isobutyrate (10 g) in methylene dichloride (35 ml) was treated with acetic anhydride (20 ml) at about 20° C. for 1 hour. Water was added and the methylene dichloride solution washed with sodium bicarbonate solution and water and dried. Evaporation to dryness and crystallisation from ether-methanol gave the title compound (6.2 g).

Using propionic anhydride instead of acetic anhydride the corresponding 3-isobutyrate 17-propionate was obtained.

(b) Quaternarisation of 2β,16β-dipiperidino-5α-androstane-3α,17β-diol 3-isobutyrate 17-acetate in a similar way as described in Example II gave the following compounds:

2β,16β-dipiperidino-5α-androstane-3α,17β-diol 3-isobutyrate 17-acetate di-ethobromide;
2β,16β-dipiperidino-5α-androstane-3α,17β-diol 3-isobutyrate 17-acetate di-allylobromide.

(c) Quaternarisation of 2β,16β-dipiperidino-5α-androstane-3α,17β-diol 3-isobutyrate 17-acetate and the corresponding 17-propionate in a similar way as described in Example II gave the following 16-monoquaternary compounds:

N-methyl-N-(3α-isobutyroxy-17β-acetoxy-2β-piperidino-5α-androstan-16β-yl)piperidinium bromide;
N-ethyl-N-(3α-isobutyroxy-17β-acetoxy-2β-piperidino-5α-androstan-16β-yl)piperidinium bromide;
N-allyl-N-(3α-isobutyroxy-17β-acetoxy-2β-piperidino-5α-androstan-16β-yl)piperidinium bromide; and the corresponding 17β-propionates; and the following 2,16-bis-quaternary compounds:

2β-(1'-methyl-1'-piperidino)-16β-(1''-ethyl-1''-piperidino)-5α-androstane-3α,17β-diol 3 isobutyrate 17-acetate dibromide;
2β-(1'-methyl-1'-piperidino)-16β-(1''-allyl-1''-piperidino)-5α-androstane-3α,17β-diol 3-isobutyrate 17-acetate dibromide;
2β-(1'-allyl-1'-piperidino)-16β-(1''-ethyl-1''-piperidino)-5α-androstane-3α,17β-diol 3-isobutyrate 17-acetate dibromide;
2β-(1'-allyl-1'-piperidino)-16β-(1''-methyl-1''-piperidino)-5α-androstane-3α,17β-diol 3-isobutyrate 17-propionate dibromide;
2β-(1'-ethyl-1'-piperidino)-16β-(1''-methyl-1''-piperidino)-5α-androstane-3α,17β-diol 3-isobutyrate 17-propionate di-iodide.

| Physical data of the compounds | | | | | |
|---|---|---|---|---|---|
| Compound ($R_1$ = isobutyryl) | | | | Physical data | |
| $R_2$ | $R_3$ | $R_4$ | X | M.p. (°C.) | $[\alpha]_D^{20}$ |
| ethyl | ethyl | H(β-isobutyroxy) | Br | 182–187 | +27,3° (a) |
| allyl | methyl | H(β-isobutyroxy) | Br | 208–215 | +29,7° (a) |
| allyl | ethyl | H(β-isobutyroxy) | Br | 170–173 | +29,9° (a) |
| methyl | ethyl | H(β-isobutyroxy) | Br | 194–200 | +38,0° (a) |
| allyl | allyl | H(β-isobutyroxy) | Br | 165–170 | +32,4° (a) |
| allyl | allyl | H(β-acetoxy) | Br | 160–166 | +29,6° (a) |
| methyl | ethyl | H(β-acetoxy) | Br | 200–205 | +16,4° (b) |
| methyl | allyl | H(β-acetoxy) | Br | 170–176 | +40,0° (a) |
| allyl | ethyl | H(β-acetoxy) | Br | | +16,4° (a) |
| — | methyl | H(β-isobutyroxy) | Br | 231–236 | −8,8° (a) |
| — | ethyl | H(β-isobutyroxy) | Br | 157–162 | −11,1° (a) |
| — | allyl | H(β-acetoxy) | Br | 175–180 | −11,6° (b) |

(a) in CHCl₃;
(b) in CH₂Cl₂

I claim:

1. Novel bisquaternary ammonium derivatives of 2β,16β-dipiperidino-5α-androstanes having the formula I:

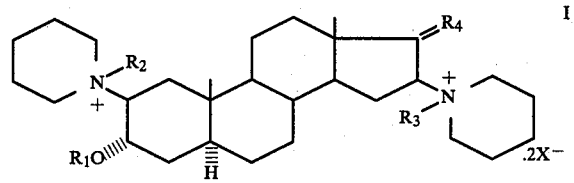

wherein
$R_1 =$

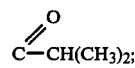

$R_2 = CH_3$, $C_2H_5$ or $CH_2CH=CH_2$;
$R_3 = CH_3$, $C_2H_5$ or $CH_2CH=CH_2$, with the proviso that $R_2$ and $R_3$ are not $CH_3$ simultaneously;
$R_4 = O$ or H(βOR₅), wherein $R_5 = H$ or aliphatic carbacyl (1-6 C); and X=a halogen atom.

2. The compounds according to claim 1, wherein $R_2=CH_2CH=CH_2$.

3. The compounds according to claim 1 or 2, wherein $R_3=C_2H_5$.

4. The compounds according to claims 1-3 wherein $R_4=H(\beta\text{-acetoxy})$.

5. The compounds according to claims 1-4, wherein $X=Br$.

6. Pharmaceutical preparations having neuromuscular blocking activity comprising a pharmaceutically effective amount of one or more compounds of claim 1.

* * * * *